(12) United States Patent
Cuypers et al.

(10) Patent No.: US 9,452,073 B2
(45) Date of Patent: Sep. 27, 2016

(54) IMMOBILIZATION DEVICE

(75) Inventors: Steven Cuypers, Gravenwezel (BE); Bogdan Bogdanov, Schoten (BE)

(73) Assignee: ORFIT INDUSTRIES, Wijnegem (BE)

( * ) Notice: Subject to any disclaimer, the term of this patent is extended or adjusted under 35 U.S.C. 154(b) by 754 days.

(21) Appl. No.: 13/634,993

(22) PCT Filed: Mar. 15, 2010

(86) PCT No.: PCT/EP2010/053313
§ 371 (c)(1),
(2), (4) Date: Dec. 3, 2012

(87) PCT Pub. No.: WO2011/113473
PCT Pub. Date: Sep. 22, 2011

(65) Prior Publication Data
US 2013/0072839 A1    Mar. 21, 2013

(51) Int. Cl.
| | |
|---|---|
| A61F 5/01 | (2006.01) |
| A61F 5/058 | (2006.01) |
| A61F 5/37 | (2006.01) |
| A61F 13/04 | (2006.01) |
| B82Y 30/00 | (2011.01) |
| C08J 5/00 | (2006.01) |

(52) U.S. Cl.
CPC ............... *A61F 5/01* (2013.01); *A61B 90/14* (2016.02); *A61B 90/18* (2016.02); *A61F 5/05841* (2013.01); *A61F 5/37* (2013.01); *A61F 13/04* (2013.01); *B82Y 30/00* (2013.01); *C08J 5/005* (2013.01); *C08J 2300/22* (2013.01); *Y10T 428/1372* (2015.01)

(58) Field of Classification Search
CPC ...... A61F 5/01; A61F 5/0102; A61F 5/0104; A61F 5/0106; A61F 5/0107; B82Y 30/00; Y10T 428/1372
USPC ......................................... 428/36.4
See application file for complete search history.

(56) References Cited

U.S. PATENT DOCUMENTS

| | | | | |
|---|---|---|---|---|
| 3,692,023 A | * | 9/1972 | Phillips et al. | .......... 602/7 |
| 2007/0004993 A1 | † | 1/2007 | Coppens | |
| 2008/0200600 A1 | * | 8/2008 | Schomaker et al. | .......... 524/445 |

FOREIGN PATENT DOCUMENTS

| | | |
|---|---|---|
| EP | 0 401 883 A1 | 12/1990 |
| WO | 96/11226 A2 | 4/1996 |
| WO | 2008/105575 A1 | 9/2008 |

OTHER PUBLICATIONS

International Search Report of PCT/EP2010/053313 dated Jun. 16, 2010.
Damien M. Marquis, Properties of Nanofillers in Polymer, 261-284, 2011, InTech.†
Michael Alexandre, Polymer-layered silicate nanocomposites: preparation, properties and uses of a new class of materials, 1-63, 2000.†

* cited by examiner
† cited by third party

*Primary Examiner* — Walter B Aughenbaugh
(74) *Attorney, Agent, or Firm* — Sughrue Mion, PLLC (57) ABSTRACT

The present invention relates to an immobilization device for immobilizing a body part, the immobilization device comprising a sheet of a thermoplastic material which has been shaped to conform to the body part to be immobilized. The thermoplastic material contains at least one nano filler material which is exfoliated.

18 Claims, 2 Drawing Sheets

IMMOBILIZATION DEVICE

CROSS REFERENCE TO RELATED APPLICATIONS

This application is a National Stage of International Application No. PCT/EP2010/053313 filed Mar. 15, 2010, the contents of all of which are incorporated herein by reference in their entirety.

The present invention relates to an immobilization device for immobilizing a body part, the immobilization device comprising a sheet of a thermoplastic material which has been shaped to conform to the shape of the body part to be immobilized, according to the preamble of the first claim.

BACKGROUND OF THE INVENTION

The use of fixation and immobilization devices or templates for immobilizing a part of a body has become well known technology in applications such as orthotics and prosthetics, physical rehabilitation, and radiation oncology and diagnostic imaging. Those applications, in particular physical rehabilitation, require that the immobilization device is mouldable at activation temperature directly on a patient, that the immobilization device shows good mechanical properties and surface finishing and is light and comfortable to the patient. For radiation oncology it is desired that the device is transparent to the radiation and that the target part may be immobilized in a precise and reproducible position with respect to the irradiation source, thereby leaving limited possibility to the immobilized body part to move with respect to the irradiation source. In particular when high precision treatments—for example in Intensity Modulated Radiation Therapy, in Image Guided Radiation Therapy, in Stereotactic Radiation Therapy or Surgery—, or treatments with high energy, for example proton therapy, are involved where the target is very well defined and delineated, the immobilization device should permit precise, highly accurate and reproducible re-positioning of the anatomical area of interest, and assure a limitation of movement of less than 2 mm to ensure that the radiation is delivered to the target, at minimum risk to exposure of surrounding healthy tissue. Other applications for immobilization devices include physical rehabilitation applications and orthopedic applications for example in splints and braces, to immobilize and protect inflamed or injured joints, to support and immobilize ligaments and fractures and muscular structures and podiatry for example as insole (foot-bed) applications.

To produce fixation or immobilization devices, which are suitable for use in the above described applications, usually use is made of a sheet shaped thermoplastic material, which is molded to conform as good as possible to the body part that is to be immobilized. With high melting thermoplastics, a positive mould is used in the shape of the part that needs to be immobilized. Over the years, continuous development has been going on towards materials, which meet specific requirements of the envisaged application. The use of sheets of thermoplastic materials which may be directly moulded to the body part to be immobilized has achieved significant attention, as this permits achieving immobilization with the highest accuracy, where the size and shape of the immobilization device may be directly adapted to each individual patient in the position in which the body part is to be immobilized, and it may be adapted in the course of time by re-moulding the immobilization device. To permit this direct moulding, the thermoplastic material should have a melting temperature which is sufficiently low to be sustained by the body. Besides that the material should have sufficient formability and elasticity in the molten state, for a period of time which is sufficiently long to permit moulding, but not too long to save clinical time and minimize the risk to deformation after moulding has been completed. A thermoplastic material which is particularly suitable for direct moulding to a body part is $\epsilon$-polycaprolactone. In practice, the $\epsilon$-polycaprolactone sheet is heated in a warm water bath, for a period of time sufficiently long to achieve softening and melting of the material, the sheet is then applied to the body part to be immobilized, shaped to conform to the body part and allowed to cool.

Immobilization devices or templates made of these thermoplastic materials need to have a certain thickness to provide the required mechanical properties. In particular the material should have a bending modulus which is sufficiently high to minimize the risk to deformation of the device and the ability of the body part to move. The material should also provide a high stability during use of the immobilization device, stability meaning the restriction to move the body parts with respect to the immobilisation device or the radiation source, when immobilised by the immobilisation device. The higher the stability, the more difficult it will be to move the body parts in the immobilised condition. To improve comfort and permit evaporation of moisture through the material, the material has been perforated. The presence of perforations however reduces rigidity of the material and stability of the device.

Furthermore, thermoplastics shrink upon crystallization when cooling down from the melting temperature. This shrinking often results in a too tight fitting after cooling and crystallization, as the immobilization device is usually already moulded to fit closely to the body part that needs immobilization. In the course of the hours or days which follow moulding and crystallization, the thermoplastic material may show annealing, which often is associated with further shrinking. The result may be a device which fits too tightly, thus rendering the contact between the inner surface of the immobilization device and the patient uncomfortable. The degree of shrinking upon crystallization usually depends on the nature of the material, as well as on the geometrical design and size of the template.

To improve comfort to the patient, U.S. Pat. No. 3,957,262 discloses the use of a headpiece in the form of a cap which receives and supports the back of the patient's head that is not to be examined. The patient's head is restrained in a certain position within the cap by means of a chin restrainer and forehead restrainer. The interior of the headpiece is made of soft rubber foam which conforms to the size and shape of the back of the patient's head to be sustained by it. As a result, some movement within the headpiece will be possible and may be permitted, but accurate re-positioning cannot be guaranteed. No means are provided which permit adapting shape and dimensions of the cap to varying dimensions of the body part over time.

In another attempt to reduce discomfort provided by the immobilization device, the weight of the thermoplastic material has been reduced by reducing the density of the material, by using foamed thermoplastic materials. According to WO9611226 to (from?) Orfit Industries, incorporation of 2-6 wt. % of expanded polymer microspheres in epsilon-polycaprolactone, permitted reducing weight per volume unit in comparison with pure epsilon-polycaprolactone based thermoplastic sheets. The material appeared to be very well mouldable, showed good surface finishing and provided good comfort to the patient. However, loss of bending modulus to about 400 MPa had to be accepted.

In a further attempt to improve stiffness and stability, EP-A-1.582.187 discloses a hybrid mask with a first part which is intended to cover the body part to be immobilized. This first part is made of a thermoplastic material which takes the shape of a web or a net with a plurality of holes to allow evaporation of moisture from the skin. Along the edges of the first part, double material thickness is used to locally increase the bending modulus, with the purpose of improving the stability of the mask. The edges of the first part are connected to fasteners to permit mounting the mask to a positioning table for the patient. The thickness of the thermoplastic material varies between 1-5 mm, preferably between 2-4 mm depending on the envisaged rigidity, stiffness and stability, and on the porosity or number and size of the perforations.

Practical examples of immobilization devices are often made of a thermoplastic sheet with a thickness of 1.6-4.2 mm. When analyzing problems encountered with existing immobilization devices and thermoplastic materials used to produce those, it became clear that attempts to improve immobilisation resulted therein that sheet materials have been developed with reduced density, to permit increasing the thickness of the thermoplastic material to obtain a higher bending or flexural modulus and improve the stability, without giving in too much on comfort to the patient.

There is thus a need for an immobilisation device, which provides improved comfort to the patient, without however giving in on the mechanical properties. On the other hand, there is still a need for immobilization devices with improved mechanical properties.

BRIEF DESCRIPTION OF THE INVENTION

It is therefore an object of the present invention to provide an immobilization device for immobilizing one or more parts of a body, which shows an improved stability, but which is still sufficiently comfortable to a patient. With stability is meant in the framework of this invention, the restriction to move the body parts with respect to the immobilisation device or the radiation source, when in the immobilised condition. With immobilized condition is for example meant a condition where the device covers a body part and is fastened or fixed to a support surface. With existing devices this has been limited to 1.5-5 mm. In particular with stability is meant the restriction of the immobilized part of the body to wobble with respect to the immobilization device and fixation plate/table or irradiation source.

In particular the invention seeks to provide an immobilization device which may be produced by direct moulding of a thermoplastic sheet material to the part of the human body that needs to be immobilized, whereby the immobilization device should be particularly suitable for use in medical applications such as orthotics and prosthetics, physical rehabilitation, and radiation oncology.

An immobilization device with improved stability is achieved according to the present invention with the technical features of the characterizing portion of the first claim.

Thereto, the immobilization device is characterized in that the thermoplastic material contains at least one nano filler material, which is exfoliated.

Within the scope of this invention the wording exfoliated means exfoliated or disaggregated, depending on the nature of the nano filler material.

The inventors have observed that by incorporation of the nano filler material in the thermoplastic material in such a way that the nano filler material is exfoliated, the bending or flexural modulus of the composite sheet material could be significantly increased, often up to a factor 2. This is important for immobilization devices, as in that way an immobilization device with a better stability may be obtained. Especially in radiation therapy stability of the immobilization device is an issue, since radiation needs to be concentrated to the target, irradiation of surrounding tissue needs to be reduced to a minimum, and therefore the possibility to move or wobble parts of the immobilization device should be reduced to a minimum.

The fact that the flexural modulus could be increased permitted to reduce the sheet thickness of the composite thermoplastic sheet, without having to compromise on the stability of the immobilization device that is required in this kind of applications, and on the mechanical properties. The thickness of the thermoplastic sheet used to produce the immobilization device can be reduced in such a way that it is no more than 80%, often no more than 60% of the thermoplastic material which is free of filler material. This permits saving on raw material and energy consumption during production. In the prior art, thermoplastic sheets used for the production of immobilization devices usually had a thickness of about 2-4.2 mm. With the present invention, the thickness of the thermoplastic sheet can be reduced to about 1.6 mm, or 1.4 mm, often to about 1.2 mm, thereby achieving a stability and flexural modulus which is at least as good as, often still better than that of the non-filled thermoplastic material.

The reduced sheet thickness in turn results in an improved transparency of the material for irradiation, in particular X-rays. The inventors observed that the presence of nano filler material in the concentrations proposed, does not affect the X-ray transparency in comparison with a free of filler material with the same thickness. This solves the problem presented by existing immobilization devices, the material of which often absorbed too much irradiation, thereby reducing the efficiency of the treatment and giving rise to a secondary electron irradiation effect which can damage the skin.

The inventors have further observed that the abrasive and scratch resistance of the thermoplastic material can be significantly improved by addition of the nano filler, which will improve life span and quality of the surface of personally moulded immobilization devices. This is of particular advantage in applications such as splints used for the immobilization of arms, legs, hands, feet and parts thereof, as they may be subjected to severe conditions during use.

A further problem that can be solved in comparison to existing immobilization devices is that by the presence of an exfoliated nano filler material, the degree of shrinking of the immobilization device upon cooling and crystallization from the molten state can be reduced, which will be sensed as an important improvement in relation to comfort, since in this way the shrinking force is reduced. Although some shrinking occurs, the degree of shrinking appears to be less than that of the non-filled thermoplastic material. In particular, the degree of shrinking could be reduced with 30-40% as compared to the non-filled material. This is an advantage, since the immobilization device is usually moulded in such a way that it closely fits the body part that needs immobilization. Shrinking which occurs upon and after crystallization often has the effect that the immobilization device, when made to fit in molten condition, may fit too tightly, provide discomfort and be painful. In addition to that, it has been found that the risk to further shrinking which usually occurs during annealing upon storage of the immobilization device, is reduced as well. This is important since the immobilization device is usually moulded to fit quite tightly to the body part to be immobilized. The present invention thus permits reducing the degree of shrinking and the shrinking force exerted by the immobilization device, while maintaining and often improving the stability or fixation force exerted by the device.

The at least one nano filler material is preferably selected from the group of organically modified minerals with a layered, lamellar structure, organically modified minerals with a multi wall tubular structure, multi wall carbon nanotubes, and mixtures of two or more of these materials.

The thermoplastic material preferably contains between 1 and 15 wt. % of organically modified clay as a layered, lamellar nano mineral, preferably between 2 and 10 wt. %, more preferably between 3 and 5 wt. % mineral nano material with respect to the weight of the thermoplastic matrix. By using mineral nano filler material in the above given concentrations, optimum exfoliation of the nano particles and uniform dispersion thereof in the thermoplastic material can be achieved. This is important to permit achieving uniform mechanical properties of the material. At concentrations below 1 wt. % the effect on the flexural modulus decreases. At concentrations above 10 wt. % the viscosity of the mixture thermoplastic material—clay nano filler increases to values where the mixture becomes more and more difficult to handle and—process, the transparency to X-rays decreases and increasing nano filler concentrations do not necessarily result in a further improvement of the mechanical properties. With increasing concentrations of nano clay filler material, also the transparency of the material as such decreases, in case use is made of transparent thermoplastic. For example, ϵ-polycaprolactone is transparent in the molten state, this is important to register optimal moulding temperature.

The increase in viscosity which occurs upon mixing of the nano filler material is attributed to the dispersion and exfoliation of the nano filler material, as a result of which a fine distribution of exfoliated nano particles in the thermoplastic material is formed. The amount of nano filler to be incorporated to achieve the desired stability and mechanical properties depends on the nature and compatibility of the nano filler and the thermoplastic material, the thickness of the composite thermoplastic sheet, the nature of the application etc. Similarly the concentration of the nano filler material that can be incorporated into the thermoplastic material depends on the nature of the nano filler material and the nature of the thermoplastic polymer.

The thermoplastic material preferably contains between 0.01 and 10 wt. % of carbon nano tubes, preferably between 0.1 and 5 wt. %, with respect to the weight of the thermoplastic material. The amount of nano carbon tubes that need to be incorporated to achieve the desired effect and the concentration that can be incorporated, depends on the nature of the nano filler material, the nature of the thermoplastic polymer and the compatibility of the two materials. At concentrations below 0.5 wt. % the effect on the flexural modulus decreases, at concentrations above 3 wt. % the viscosity of the mixture thermoplastic material—nano filler increases to values where the mixture becomes more and more difficult to handle and process. At concentrations above 7 wt. %, sometimes above 5 wt. %, increasing the carbon nano tube content does not necessarily result in a further improvement of the mechanical properties.

The inventors have observed that thermoplastic sheets which contain carbon nanotubes, are heat conductive and electrically conductive. The electrical conductivity has been found to depend on nature and concentration of the carbon nanotubes, the nature of the thermoplastic material, and the degree of dispersion of the carbon nano particles in the thermoplastic material. Because of the electrical conductive properties, a thermoplastic sheet containing dispersed carbon nano particles can be heated in a direct way, by applying an electrical current. The advantage of using direct heating or of heating the thermoplastic sheet in a dry way which does not make use of a hot water bath, but which in stead takes place for example in a gas atmosphere, for example air, in an oven or using microwave, is that the time left for moulding the thermoplastic sheet may be prolonged. A thermoplastic sheet which is heated in a water bath appeared to present faster cooling and crystallization.

Where there is a need to control the crystallisation rate of the composite thermoplastic material, a mixture of two or more thermoplastic materials may be used to produce the thermoplastic sheet material. The nano particles are thought to function as crystallisation nuclei, thereby increasing the crystallisation rate of the thermoplastic material in which they are dispersed. Depending on the nature of the envisaged application, there may be a need either to accelerate crystallisation, or to slow down crystallisation. With personalised immobilisation devices there will usually be a need to slow down crystallisation of the composite thermoplastic material in order to leave sufficient time for moulding after the material had been heated to soften and/or melt. The person skilled in the art will be capable of selecting the appropriate mixture of thermoplastic polymers to achieve the desired crystallisation rate. If use of a mixture of thermoplastic materials is considered, preferably however at least one of the materials is ϵ-polycaprolactone.

The thermoplastic sheet containing the nano filler material has a flexural flexural modulus of at least 650 MPa, preferably at least 750 MPa, more preferably at least 1000 Mpa or more. However, the flexural modulus will usually depend on the concentration and nature of the nano filler material, and the nature of the thermoplastic material. According to the present invention, the flexural modulus is measured according to ASTM method nr D790.

DETAILED DESCRIPTION OF THE INVENTION

Within the framework of this invention, a nano filler is a material with a high aspect ratio, i.e. length to diameter ratio, or a high surface to thickness ratio.

Materials suitable for use as nano filler include minerals, which have a layered, lamellar structure or a layered tubular structure. Examples of layered, lamellar mineral materials include layered silicates, mixed aluminium oxide-silicium dioxide minerals for example clays, in particular phyllosilicates for example montmorillonite, nontronite, beidelite, volkonskoite, hectorite, saponite, sauconite, magadiite, medmonite, fluoro-hectorite, vermiculite, kaolinite. Nano clays are for example available from Süd Chemie, who use the name "Nanofil" to market montmorillonite-based nanoclay, for example "Nanofil 15" and "Nanofil 5" which have been organically intercalated with distearoyldimethylammonium chloride; from the US company Elementis Corp. with the name "EA 108" based on hectorite; from Southern Clay in particular Cloisite; Bentone is available from Elementis Specialties; Laviosa Chimica Mineraria in particular Dellite. The wording "nanoclay" or "nano mineral materials" is understood to mean organically intercalated phyllosilicates or layered silicates, respectively layered minerals. This corresponds to the interpretation generally used in this technical field.

In the use of the above described nano fillers with thermoplastic materials, the naturally occurring or synthetic minerals or phyllosilicates first have to be rendered organophilic, so that they can be processed with hydrophobic thermoplastic materials, and so that exfoliation is achieved. Modification means that the mineral is modified to provide intercalation, whereby a sufficient enlarged gallery spacing between the layers or tubes is provided to permit the material to disperse or exfoliate in the thermoplastic material when subjected to shear. Intercalation may also have the effect that part of the polymeric material is capable of penetrating the layered structure.

With exfoliation is meant that the layered structure of the mineral material, aggregates of nano mineral platelets or lamellae separate from one another and become dispersed in a plastic matrix. During exfoliation platelets at the outermost region of each stack of platelets cleave off, thereby exposing more platelets for separation. During exfoliation the fillers are reduced to the state of sheets with a thickness of the order of the magnitude of a few nanometers.

The above described mineral materials may contain alkali cations such as $K^+$ or $Na^+$, alkaline-earth cations, or organic cations for example alkyl ammonium or alkyl sulphonium cations obtained by ion exchange reactions, between their lamellae. Cation exchange is usually carried out in an aqueous phase with cationic surfactants based on ammonium surfactants, or on phosphonium surfactants, or on sulfonium surfactants. Another known process is acid activation. This uses hydrochloric acid, for example.

The above defined mineral materials may also be modified with an organic compound to provide an intercalated structure. Suitable organic compounds for the organically modified nano filler include alkyl ammonium compound, preferably an alkyl ammonium compound in which the alkyl group contains at least 14 carbon atoms. More preferably, the alkyl ammonium compound contains one or more functional groups, selected from the group of OH, COOH, alkyl, aryl groups, or two or more of those. The presence of quaternary alkyl ammonium salts gives the layered mineral, in particular clay, swelling properties in organic liquids with low shear rates. The organic compound may be applied according to any method known to the skilled person, for example using ion exchange with quaternary ammonium salts, but other methods may be used as well. Mineral materials may also be modified with various polymers, such as polyvinyl alcohol (PVA) or polyacrylic acid, as described in the document U.S. Pat. No. 5,552,469, or by polyvinylpyrrolidon (PVP), or polyesters such as polyethylene terephthalate (PET) as described in the document U.S. Pat. No. 5,578,672. A sufficient quantity of polymer is absorbed between the sheets of these clays so as to space them apart by about 10 to 55 angstroms. These fillers can then be incorporated into thermoplastic materials, such as polyamides or polyesters, and after compounding, they may be exfoliated or finely dispersed, as described in the document U.S. Pat. No. 5,760,21. The nano filler material may also be intercalated with a multiblock copolymer having structural units (A) compatible with the clay and structural units (B) compatible with the matrix polymer. Clays may also be modified by a coupling agent of the silane type and co-intercalation of onium ions, as is disclosed in U.S. Pat. No. 6,407,155.

The organic compound used to organically modify the nano filler material, may be a compound with a higher or lower polarity. In the present invention, preferably organic compounds with a higher polarity are used, since this permits achieving a better dispersion degree within the thermoplastic material and a better degree of exfoliation, which gives rise to an increased stiffness of the nano composite material.

The concentration of the organic compound in the nano filler material may vary within wide ranges, but preferably vary from 30 wt. % to 70 wt. % of organic compound with respect to the weight of the nano filler, more preferably between 30 and 40 wt. %.

Where necessary, besides the intercalation compound, the nano filler material may also be surface modified to improve the compatibility with the thermoplastic polymer, with the purpose of improving dispersion. Surface modification may for example include coating the surface of the nano particles with a polymer, which is compatible with the thermoplastic polymer in which the nano filler material is to be dispersed. The nano filler material may for example be surface coated with a polymer which is the same as or differs from the thermoplastic polymer in which the nano filler material is to be dispersed. The nano filler material may for example be coated with polyethylene, polypropylene or ∈-polycaprolactone.

The interactions occurring between the nano filler and the thermoplastic material are determined by the nature of the organic compound used for providing the intercalated structure, in particular the nature and composition of the hydrocarbon backbone and the functional groups present thereon; by the nature of the nano material as such, in particular the ionic sites present on the surface of the nano filler material and by the nature of the thermoplastic material.

Another material suitable for use as nano filler includes carbon nanotubes, which are in fact one of the allotropic forms of carbon, which may be seen as one or more leaflets of graphite rolled into a cylinder and sealed at the ends. Carbon nanotubes may be composed either of a single wall—so called single-wall nano tubes, or they may be double walled or multi-walled nano tubes, depending on whether the nanotubes consist, respectively, of one, two or several leaflets. This terminology is well known to those skilled in the art. Carbon nano tubes are available from Nanocyl, Bayer Material Science, Arkema (Graphistrenght), Cheap Tubes Inc and CNT Co. The carbon nanotubes may either be pure, partly purified, crude or functionalized. The crude nanotubes may contain by-products such as amorphous carbon, pyrolytic carbon, carbon nanoparticles, carbon onions, fullerenes, metal nanoparticles encapsulated in carbon, carbon fibres, that could not be eliminated during the purification. To ensure that the advantageous properties of carbon nanotubes are transferred to the nanocomposite material, the natural aptitude of carbon nanotubes to aggregate together in very stable packets or "bundles" needs to be overcome, to permit achieving a sufficient dispersion or distribution of the carbon nanotubes in the thermoplastic material. With "optimum dispersion of nanotubes in the thermoplastic material" is meant a dispersion of nanotubes in the thermoplastic material such that the surface area of contact between two carbon nanotubes is less than 25% of the total surface area of the nanotubes, preferably less than 15%, preferably less than 10%, less than 5% and preferably less than 1% of the total surface area of said nanotubes.

Carbon nano tubes suitable for use with this invention may be functionalized with one or more organic compounds or not. Where necessary, the nano carbon filler material may be surface modified to improve the compatibility with the thermoplastic polymer, with the purpose of improving dispersion. Surface modification may for example include coating the surface of the nano particles with organic functional groups, which are compatible with the thermoplastic polymer in which the nano carbon filler material is to be dispersed. Surface modification may also include coating the nano carbon filler material with polyethylene, polypropylene or ϵ-polycaprolactone.

Examples of thermoplastic materials suitable for use in this invention include thermoplastic elastomers, thermoplastic polyurethane, thermoplastic polyisoprene, thermoplastic polyesters, thermoplastic polyolefins, polyvinylchloride, polystyrene, or a blend of two or more of these materials. Examples of suitable thermoplastic polyolefins include polyethylene, polypropylene or ethylene-propylene copolymers, but also thermoplastic elastomer which are a copolymer of ethylene with at least one α-olefin having 3-10 carbon atoms, or a blend of two or more of such copolymers, preferably copolymers of ethylene with 1-butene or a copolymer of ethylene with 1-octene or a blend of two or more of these copolymers. Examples of suitable polyesters include poly-ethylenevinylacetate, polyacrylate or polymethacrylate, polymeric fatty acid esters in particular poly-ϵ-caprolacton. Poly-ϵ-caprolacton is for example available from Perstorp (UK) as Capa. Preferably however use is made of thermoplastic polyurethane, isotactic polypropylene for its stiffness and toughness, a copolymer of ethylene with 1-butene, a copolymer of ethylene with 1-octene, poly-ϵ-caprolacton, thermoplastic polyurethane containing poly-ϵ-caprolacton because of their transparency. However a blend or a combination of two or more of these materials may be used as well.

Poly-ϵ-caprolacton is particularly preferred as it has a low melting point and is mouldable at a temperature which may be sustained by the human and animal body. However, poly-ϵ-caprolacton may also be used in a blend with one or more of the afore-mentioned thermoplastic materials.

Depending on the envisaged application, thermoplastic materials may be used with a higher or lower melting point. Suitable thermoplastic materials for use in the present invention include sheets of high temperature thermoplastics with a processing temperature above 100° C., preferably between 120° C. and 180° C. Immobilization devices made of these materials may for example be intended for the immobilization of body parts of the patient. In serial production, the immobilization device may be produced using a mould having the shape of the part to be immobilized. For individual products, direct moulding of the thermoplastic sheet to the part may be recommended. Where the immobilization of body parts is envisaged, preferably use is made of a thermoplastic material with a melting temperature that is sufficiently low to permit direct moulding to the body, in particular a melting temperature which is not above 100° C., preferably between 40° C. and 90° C., more preferably between 50° C. and 80° C. Suitable materials to be so used include low melting temperature polyesters. Particularly preferred is ϵ-polycaprolactone.

The polymer composition which is used to produce the composite thermoplastic sheet and immobilization device of this invention, may be provided as the appropriate mixture containing the appropriate concentrations of nano filler material, or it may be produced from a masterbatch which contains a high concentration of the nano filler material in a thermoplastic polymer or a blend of two or more different thermoplastic polymers. This masterbatch may be blended with a further amount of the same thermoplastic material, or a different one to produce the mixture from which the sheet material for the immobilisation device is to be made.

The composite thermoplastic sheet of the present invention may be produced from the nano filler—thermoplastic polymer blend using any technique considered suitable by the skilled person. A suitable example includes flat sheet extrusion, injection moulding and pressure moulding after melt extrusion of the thermoplastic material—nano filler mixture in an extruder to produce a sheet with a predetermined width, length and thickness.

The polymer composition which contains the nano particles and is used to produce a masterbatch, a sheet material or the immobilization device may be produced according to any method considered suitable by the skilled person, as long as the technique used results in a fine and highly homogeneous distribution of the nano filler material in the polymer. This can be done in an extruder, by melting the thermoplastic material at the appropriate temperature and mixing in the nano filler. According to another suitable technique, the organically modified nano filler material is mixed with the thermoplastic polymer using melt-mixing in an extruder, at the appropriate temperature. During extrusion, the nano filler is subjected to high shear forces, which caused exfoliation and fine dispersion of the nano filler material into the thermoplastic material.

It is noted that in the immobilization device of this invention, the thermoplastic material may be used in the form of a single sheet or a plurality of aggregated sheets, which may be made of the same or different nano filler containing thermoplastic materials, the aggregated sheets being connected to each other.

The composite thermoplastic sheet will usually have a thickness which is adapted to the intended use. When used as an immobilization device for immobilizing a body part, the thickness will usually be between 0.5 and 3.2 mm, preferably between 0.5 and 2.0 mm, more preferably between 0.8 and 1.5 mm, most preferably 1.1-1.3 mm. Often a thickness of about 1.2 mm or somewhat more will be used. When selecting the appropriate thickness, the skilled person will take into account that the thickness is sufficient to provide the properties required for the intended application. For immobilization devices the thickness should be selected such that the flexural modulus and the stability or fixation force are within the required ranges for that application, and that the cooling time of the thermoplastic sheet after having been heated to soften or melt, is sufficiently long to permit moulding.

The composite thermoplastic sheet may be used as a solid sheet, but it may also comprise a plurality of perforations which extend through the thickness of the sheet. The perforated sheet is preferred as the reduced weight and evaporation possibility improve patient comfort. With perforations is meant that the thermoplastic sheet contains a plurality of holes, which extend throughout the material of the sheet. Upon moulding, the thermoplastic sheet will usually be stretched and the perforations will be stretched as well, thus increasing their dimensions. The perforations may be applied randomly or according to a specific pattern. The diameter of the perforations in the thermoplastic material will usually be between 0.5 and 3 mm, preferably 1 to 2 mm. Dimensions and pattern of the perforations will usually be chosen in such a way that heat is kept inside the device, to provide a cooling time of the material from the molten state, which is sufficiently long to permit moulding.

The present invention also relates to the use of a thermoplastic material which contains at least one nano filler material selected from the group of the at least one nano filler material is selected from the group of organically modified minerals with a layered, lamellar structure, organically modified minerals with a multi wall tubular structure, multi wall carbon nanotubes, or a mixture of two or more of these materials as described above, for the production of an immobilization device for immobilizing a body part. Thereby use can be made of a mixture of the thermoplastic material and the nano filler, or use can be made of a masterbatch containing from 95 to 70 wt. % of thermoplastic polymer and 5 to 30 wt. % of nano filler material, which masterbatch is molten and mixed with thermoplastic polymer to produce the nano filled thermoplastic material suitable for the production of sheet material from which the immobilisation devices are made.

The present invention further relates to the use of a sheet of a thermoplastic material which contains at least one nano filler material for the production of immobilization devices. With immobilization device is meant for example a splint for immobilizing a hand or part of a hand, an arm or part thereof, a leg or foot or part thereof, and for example mask for immobilizing a head or any other part of the body. The immobilisation device may however also be used for immobilising any other tool considered by the skilled person.

If so desired, the immobilization device of this invention can be made of two parts, wherein a first part which is provided to cover the body part to be immobilized is made of the above described nano filled thermoplastic material, and a second part which functions as a fastener or for mounting the first part to a support surface, is made of a non-filled thermoplastic material or any other plastic material.

The present invention further relates to a method for producing an immobilization device as described above, wherein a sheet of a thermoplastic material containing at least one nano filler material is heated to a temperature which corresponds to the melting temperature of the thermoplastic material, positioned on the body part or any other tool to be immobilized, or on a positive mold, moulded and left to cool. Thereby heating of the nano filled thermoplastic sheet can be carried out in the conventional manner, by submersion of the sheet in a warm water bath until the thermoplastic material is molten. Heating can however also be carried out using a dry heating method, whereby the nano filled thermoplastic sheet material is heated in an oven at the appropriate temperature, or using microwaves, or in a flow of a warm gas at the appropriate temperature.

Due to the presence of exfoliated nano filler material in the thermoplastic material that is used to produce an immobilization device, the mechanical properties of the thermoplastic material may be improved, in particular the bending or flexural modulus may be increased. The increased flexural modulus permits to use thermoplastic sheets with reduced thickness for the production of immobilization devices, and that way at least keep and often improve the transparency of the material towards X-rays. The increased flexural modulus of the filled thermoplastic sheet permits to obtain immobilization devices with improved stability, or on the other hand permits to reduce the thickness of the thermoplastic sheet without giving in on stability of the immobilization device. Besides that, thermoplastic materials containing nano filler material show less shrinking upon cooling and crystallization, after having been heated to the melting point. As a result the shrinking force exerted by an immobilization device which has been moulded from a molten sheet, may be reduced and comfort to the patient is improved. The incorporation of the appropriate amounts of nano filler material in thermoplastic materials as described above thus permits to produce immobilization devices with an improved stability and fixation force, while limiting the degree of shrinking and improving comfort to the patient.

The filler concentration of the nano filler material may be kept relatively low, since the filler particles are exfoliated or disaggregated and on nano scale dispersed in a polymer matrix.

The invention is further elucidated in the appending examples.

EXAMPLE 1

A composite material was produced by mixing from 0.25 to 2.5 wt. % of carbon nanotubes as indicated in table 1 below into ε-polycaprolactone Capa obtained from Perstorp UK Ltd. The following types of carbon nanotubes were used: Baytubes obtained from Bayer Material Science, and Graphistrenght obtained from Akema. Mixing was accomplished using a batch-operated lab-scale twin-screw DSM Micro Compounder (15 cc, N2 purge, screw rotation speed 170 rpm), with an extruder residence time of 30 minutes. The thus obtained composite material was compression moulded into a sheet at 140° C., 100 bar pressure, using an Agila PE30 hydraulic press.

To assess electro conductivity, 4-point conductivity measurements were performed on the surface of the nanocomposite sheet, using a Keithley 6512 programmable Electrometer (current range $1.1 \times 10^{-6}$-$1.1 \times 10^{-2}$; voltage range $10^{-4}$-100 V). A colloidal graphite paste provided by Electron Microscopy Science was employed to ensure proper contact between the sample and the measuring electrodes. The results are summarized in table 1 below.

TABLE 1

Electrical conductivity of ε-polycaprolactone Capa, containing varying types of carbon nanotubes.

| Carbon nanotube (wt. %) | Electrical conductivity ($S^{m-1}$) | Flexural Modulus (MPa) |
|---|---|---|
| 0 | 1.0E−09.25 | 500 |
| 1.5 wt. % Baytubes | 1.0E+0.75 | 615 |
| 1.5 wt. % Graphistrenght C100 | 1.0E+01 | 700 |
| 0.25 wt. % of Nanocyl 7000 | 1.0E−02.25 | |
| 0.5 wt. % of Nanocyl 7000 | 1.0E+00 | |
| 2.5 wt. % of Nanocyl 7000 | 1.0E+1.75 | |

EXAMPLE 2

A composite material was produced by mixing 5 wt. % of each of the nanofillers given in table 2, into ε-polycaprolactone obtained from Perstorp. Mixing was accomplished using a lab-scale twin-screw compounder type ZSK-18 (Coperion). Such obtained composite material was compression molded into a sheet at 140° C., 100 bar pressure, using an Agila PE30 hydraulic press.

The secant or flexural modulus was measured using a 3-point bending mode, 90 mm span, 4 mm deflection at 21° C., using a Lloyd Instruments LRX Plus apparatus. An average of three measurements was taken for each sample, measurements were performed 7 days after the composite materials had been compression moulded as described in example 1, and stored at 21° C. The sample dimensions were 130×30×1.6 mm.

| Nano material (5 wt. %) | Flexural Modulus (MPa) |
|---|---|
| ε-polycaprolactone | 500 |
| Bentone DE | 560 |
| Nanofil SE310 | 900 |
| Cloisite Na+ | 900 |

EXAMPLE 3

A composite material was produced by mixing respectively 3 and 10 wt. % of Nanofil SE3010 and Cloisite 10A, into ε-polycaprolactone Capa obtained from Perstorp UK Ltd. Mixing was accomplished using a batch-operated lab-scale twin-screw DSM Xplore Micro Compounder (15 cc, N2 purge, screw rotation speed 170 rpm), with an extruder residence time of 30 minutes. The thus obtained composite material was compression moulded into a sheet at 140° C., 100 bar pressure, using an Agila PE30 hydraulic press.

The secant modulus was measured using a 3-point bending mode, 90 mm span, 4 mm deflection at 21° C., using a Lloyd Instruments LRX Plus apparatus. An average of three measurements was taken for each sample, measurements were performed 7 days after the composite materials had been compression moulded as described in example 1, and stored at 21° C. The sample dimensions were 130×30×1.6 mm. The results are summarized in table 3.

TABLE 3

| Nano material (wt. %) | Flexural Modulus (MPa) |
|---|---|
| Nanofil SE3010, 3 wt. % | 650 |
| Nanofil SE3010, 10 wt. % | 800 |
| Cloisite 10A, 3 wt. % | 700 |
| Cloisite 10A, 10 wt. % | 960 |

EXAMPLE 4

A composite material was produced by mixing 5 wt. % of each of the materials given in table 4, into Polypropylene-co-PE obtained from DOW. Chemical Co. Mixing was accomplished using a lab-scale twin-screw ZSK-18 (Coperion) The thus obtained composite material was compression moulded into a sheet at 220° C., 100 bar pressure, using an Agila PE30 hydraulic press.

The secant modulus was measured using a 3-point bending mode, 90 mm span, 4 mm deflection at 21° C., using a Lloyd Instruments LRX Plus apparatus. An average of three measurements was taken for each sample, measurements were performed 7 days after the composite materials had been compression moulded as described in example 1, and stored at 21° C. The sample dimensions were 130×30×3.2 mm. The results are summarized in table 4.

TABLE 4

| Nano material (wt. %) | Flexural Modulus (MPa) |
|---|---|
| Polypropylene-co-PE | 1280 |
| Nanofil 5, 5 wt. % | 1570 |
| Nanofil SE3000, 5 wt. % | 1400 |
| Cloisite 15A, 5 wt. % | 1550 |

EXAMPLE 5

Figure 1:
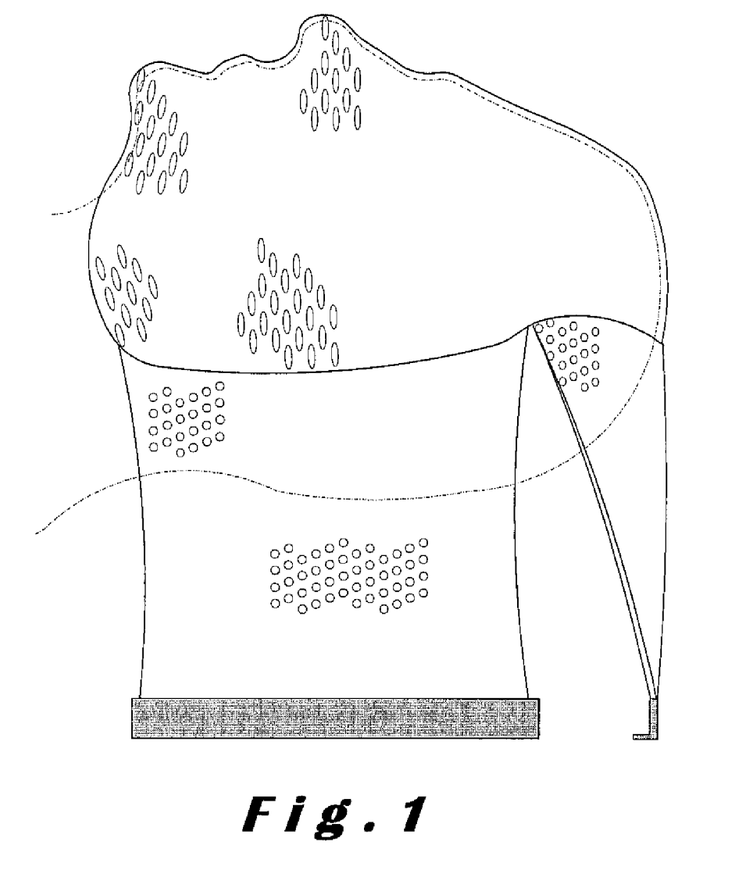
FIG. 1 shows an example of an immobilization device of the present invention, for immobilising a head.
Figure 2:
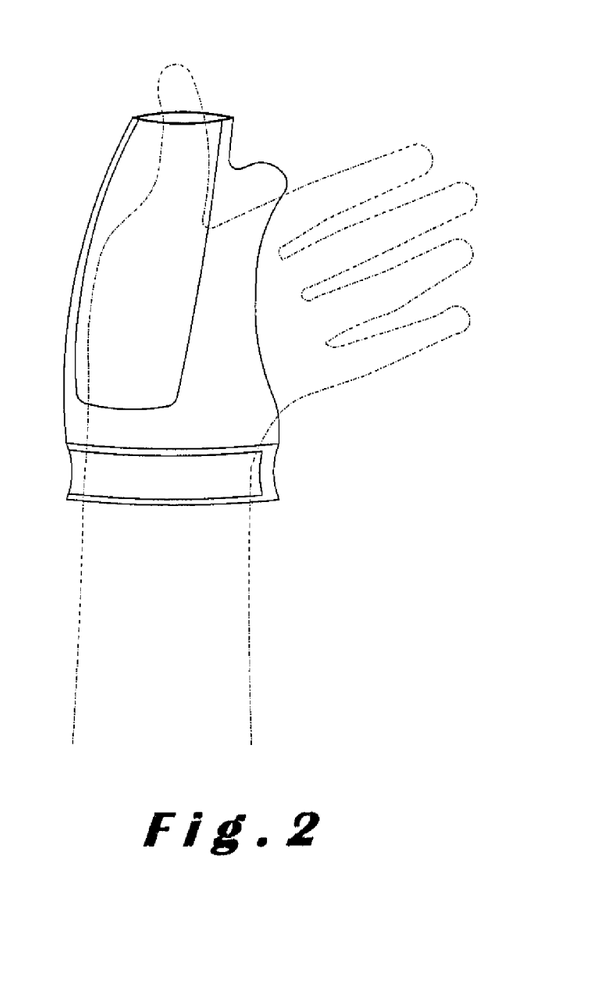
FIG. 2 shows an example of a splint, for immobilising a hand.

A thermoplastic sheet was produced by means of a industrial scale twin-screw extruder with flat die, using ε-polycaprolactone containing the nano materials given in table 5 below in the indicated concentrations. ε-polycaprolactone containing no filler was used as the reference material. Each time a sheet was produced having the thickness given in table 5. From each sheet an immobilization standard mask was produced to cover a face, as shown in FIG. 1. The stability of the thus obtained mask based on ε-polycaprolactone nanocomposite was measured as follows. A specially designed instrument, based on a method described in Belgium patent N° 1015081, 26 Aug. 2002, which can measure the shrinkage force and stability of the mask and/or to apply different fixation forces to the mask which was moulded on a dummy head was used. With the stability of fixation of the mask is meant the horizontal displacement in mm of a dummy head when a particular fixation force is applied to the mask and horizontal force of 100N is applied to the dummy head.

| Nano material | Concentration (wt. %) | Thickness (mm) | Stability (mm) | Stability Improvement (%) |
|---|---|---|---|---|
| no | 0 | 2 | 1.75 | |
| Nanofil 5 | 7 | 1.2 | 1.15 | 34.3% |
| | | 1.6 | 1.4 | 20% |
| | | 2 | 1.27 | 27.4% |
| Nanofil 5 + CNT Graphistrenght C100 | 5 wt. % + 2 wt. % | 1.2 | 1.15 | 34.3% |
| | | 1.6 | 1.07 | 61.1% |
| | | 2 | 1.27 | 27.4% |

From table 5 it can be concluded that the stability of an immobilisation device can be significantly improved by incorporation of a nano filler material. An improved stability was observed with a mask made of sheet of a nano filler material containing ε-polycaprolactone which had the same thickness as the sheet of ε-polycaprolactone which was free of filler material, but also with sheets which had a smaller thickness. Even when reducing the thickness of the sheet with 60% (1.2 mm↔2 mm), an improved stability had been observed.

EXAMPLE 6

Nano composite materials were produced according to the method of example 5 using an industrial scale extruder and Nanocyl 7000 as the nano filler material. From these sheet materials, samples of 20×50 mm were cut, with different thicknesses of 1.2 to 2 mm. The volume resistance of the thus obtained thermoplastic samples was measured using a two point electrical multi measuring instrument. A silver or graphite paste is used to improve the electrical contact between the clamps and the sample. The results are presented in table 6 below. From the results summarised in table 6 it appears that the resistance decreases with increasing thickness of the thermoplastic sheet material.

TABLE 6

| Thickness (mm) | Cross section (mm$^2$) | Resistance (kOhm) | ρ (Ohm · m) | Conductivity (S · m$^2$) |
|---|---|---|---|---|
| 1.2 | 24 | 16.83 | 8.078 | 0.124 |
| 1.6 | 32 | 10.30 | 6.592 | 0.152 |
| 2.0 | 40 | 2.267 | 1.814 | 0.551 |

The fact that the nano composite thermoplastic sheet materials are electro conductive, permits using alternative or direct current for heating and melting the sheet material, by applying a suitable voltage.

After the sheets disclosed in table 6 had been heated to the melting point and cooled, different alternating voltages were applied to the edges of the samples. From table 7 it can be seen that the resistance of the samples at room temperature decreased after first melting to 70°-80° C. followed by cooling to 21° C. Furthermore, the resistance after first melting and cooling deemed to be independent on the thickness of the sheet.

TABLE 7

| Thickness (mm) | Resistance (kOhm) | Resistance 30 minutes after melting | Resistance 40 days after melting |
|---|---|---|---|
| 1.2 | 23.8 | 1.9 | 1.6 |
| 1.6 | 12 | 1.5 | 1.3 |
| 2.0 | 2.7 | 0.64 | 0.53 |

The invention claimed is:

1. An immobilization device for immobilizing a body part, the immobilization device comprising a sheet of a thermoplastic material which has been shaped to conform to the body part to be immobilized, the thermoplastic material contains at least one nano filler material which is exfoliated, the at least one nano filler material is selected from the group of organically modified minerals with a layered, lamellar structure, organically modified minerals with a multi wall tubular structure, multi wall carbon nanotubes, and mixtures of two or more of these materials,
wherein the organically modified nano filler contains an alkyl ammonium compound.

2. An immobilization device as claimed in claim 1, wherein the thermoplastic material contains between 1 and 15 wt. % of organically modified clay, with respect to the weight of the thermoplastic material.

3. An immobilization device as claimed in claim 1, wherein the thermoplastic material contains between 2 and 10 wt. % of organically modified clay with respect to the weight of the thermoplastic material.

4. An immobilization device as claimed in claim 1, wherein the thermoplastic material contains between 3 and 5 wt. % of organically modified clay, with respect to the weight of the thermoplastic material.

5. An immobilization device as claimed in claim 1, wherein the thermoplastic material contains between 0.01 and 10 wt. % of carbon nano tubes with respect to the weight of the thermoplastic material.

6. An immobilization device as claimed in claim 1, wherein the thermoplastic material contains between 0.1 and 5 wt. % of carbon nano tubes with respect to the weight of the thermoplastic material.

7. An immobilization device as claimed in claim 1, wherein the alkyl ammonium compound is an alkyl ammonium compound in which the alkyl group contains at least 14 carbon atoms.

8. An immobilization device as claimed in claim 1, wherein the alkyl ammonium compound contains one or more functional groups, selected from the group of OH, COOH, alkyl, aryl groups and two or more of those.

9. An immobilization device as claimed in claim 1, wherein the thermoplastic sheet material is selected from the group of thermoplastic elastomers, thermoplastic polyurethane, thermoplastic polyisoprene, thermoplastic polyesters, thermoplastic polyolefins, polyvinylchloride, polystyrene and a blend or combination of two or more of these materials.

10. An immobilization device as claimed in claim 1, wherein the thermoplastic sheet material is selected from the group of thermoplastic polyurethane, isotactic polypropylene, a copolymer of ethylene with 1-butene, a copolymer of ethylene with 1-octene, poly-ϵ-caprolactone, thermoplastic polyurethane containing ϵ-polycaprolactone, and a blend or a combination of two or more of these materials.

11. An immobilization device as claimed in claim 1, wherein the thermoplastic sheet material comprises a mixture of poly-ϵ-caprolactone and a further thermoplastic material.

12. An immobilization device as claimed in claim 1, wherein the thermoplastic sheet containing the nano filler material has a flexural modulus of at least 650 Mpa.

13. An immobilization device as claimed in claim 1, wherein the thermoplastic sheet containing the nano filler material has a flexural modulus of at least 1000 MPa.

14. An immobilization device as claimed in claim 1, wherein the thermoplastic sheet comprises a plurality of perforations, which extend through the thickness of the sheet.

15. An immobilization device as claimed in claim 1, wherein the thermoplastic sheet has a thickness of between 0.5 and 3.2 mm.

16. An immobilization device as claimed in claim 1, wherein the thermoplastic sheet has a thickness of between 0.5 and 2.0 mm.

17. An immobilization device as claimed in claim 1, wherein the thermoplastic sheet has a thickness of between 1.5 and 1.75 mm.

18. An immobilization device as claimed in claim 1, wherein the thermoplastic sheet has a thickness of 1.1-1.3 mm.

* * * * *